(12) United States Patent
Coleman et al.

(10) Patent No.: US 10,793,797 B2
(45) Date of Patent: Oct. 6, 2020

(54) INTEGRATED PROCESS AND UNIT OPERATION FOR CONDITIONING A SOOT-CONTAINING SYNGAS

(71) Applicant: PRAXAIR TECHNOLOGY, INC., Danbury, CT (US)

(72) Inventors: Luke Coleman, Williamsville, NY (US); Minish Mahendra Shah, East Amherst, NY (US); Joseph Schwartz, Williamsville, NY (US); Jerome Jankowiak, Williamsville, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 0 days.

(21) Appl. No.: 15/678,564

(22) Filed: Aug. 16, 2017

(65) Prior Publication Data

US 2019/0055487 A1 Feb. 21, 2019

(51) Int. Cl.

| B01D 47/00 | (2006.01) |
|---|---|
| B01D 47/02 | (2006.01) |
| B01D 47/12 | (2006.01) |
| C10L 3/08 | (2006.01) |
| C10L 9/06 | (2006.01) |
| C10G 1/06 | (2006.01) |
| C10K 1/10 | (2006.01) |
| B01D 47/06 | (2006.01) |
| B01D 47/10 | (2006.01) |
| C07C 1/04 | (2006.01) |
| B01D 3/14 | (2006.01) |

(52) U.S. Cl.
CPC .............. *C10L 3/08* (2013.01); *B01D 47/06* (2013.01); *B01D 47/10* (2013.01); *C10G 1/06* (2013.01); *C10K 1/101* (2013.01); *C10L 9/06* (2013.01); *B01D 3/14* (2013.01); *B01D 2247/04* (2013.01); *B01D 2247/107* (2013.01); *C07C 1/0485* (2013.01)

(58) Field of Classification Search
CPC .......... B01D 47/10; B01D 47/02; B01D 47/12
See application file for complete search history.

(56) References Cited

U.S. PATENT DOCUMENTS

| 3,895,926 | A | * | 7/1975 | Lerner | ................... B01D 45/08 95/219 |
|---|---|---|---|---|---|
| 4,074,981 | A | * | 2/1978 | Slater | ..................... C01B 3/22 252/373 |
| 4,099,938 | A | * | 7/1978 | Onnen | ................... B01D 47/06 96/229 |
| 4,110,359 | A | | 8/1978 | Marion | |
| 4,149,859 | A | | 4/1979 | Vigesdal | |
| 4,189,307 | A | | 2/1980 | Marion | |
| 4,197,281 | A | * | 4/1980 | Muenger | ............... C01C 1/0488 252/375 |
| 4,591,366 | A | | 5/1986 | Wohner et al. | |
| 4,704,137 | A | | 11/1987 | Richter | |
| 5,453,115 | A | | 9/1995 | Vuletic | |
| 5,512,085 | A | | 4/1996 | Schwab | |
| 6,004,379 | A | | 12/1999 | Wallace et al. | |
| 6,083,302 | A | * | 7/2000 | Bauver, II | ............. B01D 45/08 55/440 |
| 2009/0183632 | A1 | | 7/2009 | Peltonen et al. | |
| 2011/0000779 | A1 | | 1/2011 | Kowoll | |

FOREIGN PATENT DOCUMENTS

| DE | 19751851 A1 | 5/1999 |
|---|---|---|
| EP | 0606573 A1 | 7/1994 |
| WO | 2010149173 A2 | 12/2010 |

* cited by examiner

*Primary Examiner* — Randy Boyer
(74) *Attorney, Agent, or Firm* — Iurie A. Schwartz

(57) ABSTRACT

The present invention relates to a method for conditioning a soot-containing syngas stream in a single integrated apparatus containing a scrubbing vessel wherein particulate matter is decoupled from the waste water stream.

11 Claims, 4 Drawing Sheets

INTEGRATED PROCESS AND UNIT OPERATION FOR CONDITIONING A SOOT-CONTAINING SYNGAS

BACKGROUND OF THE INVENTION

Field of the Invention

The present invention relates to a method for conditioning a soot-containing syngas stream in a single integrated apparatus containing a scrubbing vessel wherein particulate matter removal is decoupled from the waste water stream. More specifically, the process and apparatus of the invention is compact, less complex, generates fewer waste water streams and concentrates the waste product such that it can be easily handled and disposed of.

Description of Related Art

Partial oxidation based gasifiers generate synthesis gases (hereinafter, referred to as "syngas(es)")—is mixtures of $H_2$, CO, $CO_2$, $CH_4$, and $H_2O$—containing particulate matter (e.g., soot, refractory dust) and trace, undesirable by-products including ammonia ($NH_3$) and hydrogen cyanide (HCN) that must be removed prior to the syngas being further processed to produce purified hydrogen and CO or a chemical-grade syngas for fuels and chemical production. Processes for the removal of particulate matter and $NH_3$ are considered in the related art, but these processes achieve the required separation as a series of sequential separation processes essentially removing one contaminant at a time. These approaches ultimately lead to undue process complexity, numerous waste streams with differing compositions, and a high capital expense.

In a typical separation process such as the one described in U.S. Pat. No. 4,110,359 to Marion for the production of a cleaned and purified synthesis gas, requires a particulate matter scrubbing and gas cooling process. The process described is a conventional syngas scrubbing and cooling with a simplified flowsheet, as shown in FIG. 1. Entrained particulate matter is removed from the produced synthesis gas stream (36) by contacting the synthesis gas stream and a water stream (37) in an orifice or venturi scrubber (38). The gas-liquid mixture (39) is disengaged in a separation vessel (40) with the particulate matter going with the water (45) and exiting the bottom of the separation vessel. Cleaned gas (48) exits the top of the separation vessel and is cooled below the dew point in a heat exchanger (50) by indirect heat exchange with cold water (51,52). Cooled stream (53) is routed to a condensate knockout pot (54) where the condensed liquid (55) leaves through the bottom of the vessel and the cleaned, cooled synthesis gas (56) exits from the top of the vessel. The process described by Marion consists of at least 3 separate process steps (38, 39, 50, 56) and generates two wastewater steams (45, 55).

U.S. Pat. No. 4,189,307 to Marion describes a process for the production of a clean, HCN-free syngas. A cooled, particulate-laden syngas stream having a temperature in the range of 300° F. to 900° F. is fed to a soot scrubbing column having a counter-current flow of process water entering the column operates at a temperature in the range of ambient to 250° F. to remove effectively all of the particulate matter from the syngas stream. In addition to scrubbing, the process water also cools the syngas stream to 212° F. to 600° F. The particulate-laden process water stream exits the bottom of the soot scrubber at a temperature in the range of 212 to 600° F. and is sent to a carbon separation and concentration zone. The cleaned syngas stream exits the soot scrubber and is routed to a series of at least two indirect heat exchangers to lower the temperature of the syngas stream below the dew point (ambient to 150° F.) producing a two phase stream.

Condensate is separated from the cooled and cleaned syngas in a knockout pot with the syngas being fed to a HCN-absorption zone and at least a portion of the process condensate being utilized as the process water in the soot scrubber. This Marion document teaches that the soot scrubbing column performs two roles: 1) particulate matter removal and 2) gas cooling. Further it teaches that the water-soluble contaminants such as $NH_3$ and HCN would not be effectively scrubbed from the syngas stream in the soot scrubber due to low solubility at the temperatures of the process water stream exiting the bottom of the column. As such, one skilled in the art, including the inventor of U.S. Pat. No. 4,189,307, would understand that the syngas stream exiting the soot scrubber would contain substantially all of the water-soluble contaminants. The process described in U.S. Pat. No. 4,189,307 consists of at least 4 separate process steps and generates two wastewater streams.

U.S. Pat. No. 4,704,137 to Richter further discloses a process where the quenched syngas is brought into contact with a process water stream and passed through a conventional Venturi-type scrubber to remove entrained particulate matter. The resulting gas-liquid mixture is disengaged in a separation vessel with the particulate matter going with the water and exiting the bottom of the separation vessel. The syngas stream exiting the top of the separation vessel is subsequently partitioned with a portion being sent to a series of three indirect heat exchangers coupled with three condensate knockout pots to produce a cooled syngas having a temperature in the range of ambient to 150° F. The cleaned and cooled syngas stream exits the top of the third and final knockout pot. The condensate streams from the first two knockout pots are combined and returned to the separator vessel described above as a washwater to improve particulate matter removal. The condensate from the third and final knockout pot contains water-soluble contaminants, including HCN, COS, formic acid, and mixtures thereof, which can be returned to the process, vaporized, and the contaminants converted to either more easily handled contaminants or destroyed in a conventional water-gas shift reactor. The syngas scrubbing process described in U.S. Pat. No. 4,704, 137 consists of at least three process steps and at least eight unit operations.

U.S. Pat. No. 6,004,379 to Wallace et al. discloses a system for quenching and scrubbing particulate matter and $NH_3$ from a hot partial oxidation gas stream via a multiple step system consisting of a scrubbing tower for particulate removal, a system of heat exchangers in combination with two or less knockout drums, and a water wash column for $NH_3$ scrubbing. The process described in this document performs these process steps or operations in a sequential series leading to a process requiring a minimum of three separate process vessels and generating a minimum of two process wastewater streams.

U.S. Patent Application Publication No. 2011/0000779 A1 to Kowoll describes a process in which a raw syngas obtained from the gasification of coal is scrubbed of particulate matter and partially scrubbed of water-soluble contaminants to produce a cleaned syngas. The raw syngas stream is mixed with a process water stream in a Venturi scrubber with the combined fluid stream being passed to a droplet precipitator or cyclone to disengage the particulate matter-bearing process water from the raw syngas stream. The raw syngas stream is subsequently passed to a washing tower to remove solid fine particles and partially scrub water-soluble contaminants from the syngas stream. The scrubbed syngas stream is then preheated and fed to a CO conversion device to adjusting the $H_2$/CO ratio for downstream processing. The syngas scrubbing process described by Kowoll consists of at least three separate process steps that are operated at temperatures above which the water-soluble contaminants such as $NH_3$ and HCN will not be effectively scrubbed from the syngas stream.

All of the foregoing related art discuses particulate matter removal, gas cooling, and scrubbing of water-soluble contaminants from syngas streams as a complex multi-step process performed sequentially in several process units.

To overcome the disadvantages of the related art, it is an object of the present invention to provide a process and unit operation that integrates the syngas conditioning steps of i) particulate matter removal, ii) ammonia removal, iii) process gas cooling, and iv) condensate knockout into a single process unit operation. The proposed syngas conditioning system has numerous benefits compared to the conventional process system because it performs numerous process steps in a single process vessel and decouples particulate matter removal from the waste water system which effectively eliminates a waste water stream. Additionally, indirect process gas heat exchangers for syngas cooling are replaced with direct contact cooling for syngas and highly efficient liquid-liquid heat exchangers for heat rejection which has the added benefit of reducing the capital investment and process footprint.

An additional benefit of the proposed integrated process and unit operation is a reduction in the quantity of waste water rejected from the system due to the decoupling of the particulate matter and water rejection mechanisms. In conventional processes, the concentration of particulate matter in the process water is controlled by rejecting waste water from the system. In the proposed integrated process, particulate matter removal and waste water rejection are decoupled as particulate matter is removed from the process by a mechanical means that is independent of the disposal of waste water. This has the effect of dramatically reducing the amount of waste water rejected from the process and further, a significant reduction in the amount of fresh, high-quality make up water can be realized. Reducing the quantity and complexity of the waste water stream has the benefit of simplifying and reducing the scale of the waste water treatment system.

Other objects and aspects of the present invention will become apparent to one of ordinary skill in the art upon review of the specification, drawings and claims appended hereto.

SUMMARY OF THE INVENTION

According to an aspect of the invention, integrated process for conditioning a soot-containing synthesis gas stream, comprising:

introducing a raw soot-containing synthesis gas having particulate matter and gaseous contaminants therein at a temperature of less than about 900° F. into a quenching device to reduce the temperature of said synthesis gas to a range of about 250-400° F., thereby forming a two-phase stream;

routing the two-phase stream through a first scrubber device to substantially transfer majority of particulate matter from the gas phase to the liquid phase;

directing said two-phase stream to a second scrubbing device wherein the two-phase stream is separated into a water phase fluid contaminated with particulate matter and a gas phase fluid having water-soluble contaminants at a lower section of the scrubbing device;

cleaning and cooling the gas phase fluid having water-soluble contaminants in an upper section of the second scrubbing device where the gas phase fluid comes in direct contact with cooled process water dispensed through a spray nozzle device thereby reducing the temperature of the gas phase fluid below the dew point temperature and removing water soluble impurities and remaining particulate matter therefrom;

further routing the cooled and cleaned gas phase fluid of step (d) through a mist eliminating device disposed in the upper section of the second scrubbing device to remove substantially all of the remaining entrained water droplets, thereby producing a cooled and substantially soot free synthesis gas stream.

According to another aspect of the invention, integrated unit operation for conditioning a soot-containing synthesis gas stream, comprising:

a quenching device, wherein a raw soot-containing synthesis gas having particulate matter and gaseous contaminants having a temperature of less than 900° F. is introduced and the temperature of the soot-containing synthesis gas is reduced to a temperature ranging from 250–400° F. thereby forming a two-phase stream;

a first scrubbing device for receiving the cooled two-phase stream, wherein said device is selected from the group of Venturi scrubbers, Venturi tubes, orifice plate, atomizers;

a second scrubbing device for receiving the two-phase stream where it is separated into a water phase fluid contaminated with particulate matter and a gas phase fluid having water-soluble contaminants in the lower section of the scrubbing device;

a spray nozzle device disposed in an upper section of the second scrubbing device to clean the gas phase fluid by bringing said gas phase fluid in direct contact with cooled process water dispensed through said spray nozzle device, thereby reducing the temperature of the gas phase fluid below the dew temperature and removing the water-soluble contaminants therefrom;

a mist eliminating device above the spray nozzle device in the upper section of the second scrubbing device for the removal of substantially all of the remaining entrained water droplets in the gas phase fluid rising to the top of the scrubber device, thereby producing a cooled and substantially soot free synthesis gas stream.

BRIEF DESCRIPTION OF THE FIGURES

The objects and advantages of the invention will be better understood from the following detailed description of the preferred embodiments thereof in connection with the accompanying figures wherein like numbers denote same features throughout and wherein.

DETAILED DESCRIPTION OF THE INVENTION

The present invention provides for the conditioning (or cleaning) of a syngas stream generated from a steam methane reformer, partial oxidation unit, auto thermal reformer or combinations thereof processing a hydrocarbon containing feedstock. The syngas stream generated is typically a mixture of $H_2$, CO, $CO_2$, $CH_4$, $H_2O$, that contains particulate matter (e.g., soot, refractory dust, etc.) and trace, undesirable contaminants including ammonia ($NH_3$) and hydrogen cyanide (HCN) that must be removed prior to being further processed to produce purified hydrogen and CO or a chemical-grade syngas for fuels and chemical production.

Particulate matter (referred, at times, simply as "PM") must be removed from the produced syngas to eliminate the potential for eroding and clogging process equipment including heat exchangers, piping, process valves and critical safety equipment such as pressure relief valves. If not substantially removed prior to cooling the syngas stream below its dew point, PM will contaminate produced condensate streams and potentially enter the process water streams, which are commonly reused in numerous process operations. Further, PM is a known cause for foaming and flooding in downstream processes such as $CO_2$ scrubbing units that can lead to poor unit operation and ultimately costly plant outages. Water-soluble contaminants including $NH_3$, HCN, CHOOH, HCl, $H_2S$, COS, are produced during the production or processing of syngas via undesirable reactions. These species must be removed from the syngas before final process as they are contaminants or poisons to downstream process units.

The present invention has application to hot raw soot-containing syngas streams with a temperature in the range of about 300 to 900° F., and preferably 350° F. to 600° F. The pressure of these streams can range from about 1 to 600 psig, and preferably 300 to 500 psig. The gas composition of the hot raw syngas stream by volume on a dry basis is typically: 50 to 75% $H_2$, 20 to 45% CO, 1 to 10% $CO_2$, 0.1 to 5% $CH_4$, 0-1% $N_2$, 0-1% Ar, 0-1% of small hydrocarbons including, for example, $C_2H_2$, $C_2H_4$, $C_2H_6$, $C_3H_6$, 0 to 500 ppmv $NH_3$, 0 to 100 ppmv HCN, 0 to 10 ppmv $H_2S$, and 0 to 5 ppmv COS. The raw syngas stream may also contain 0 to 500 $mg/Nm^3$ of particulate matter consisting primarily of soot derived from the hydrocarbon feedstock and refractory dust originating from upstream process equipment.

Figure 1:
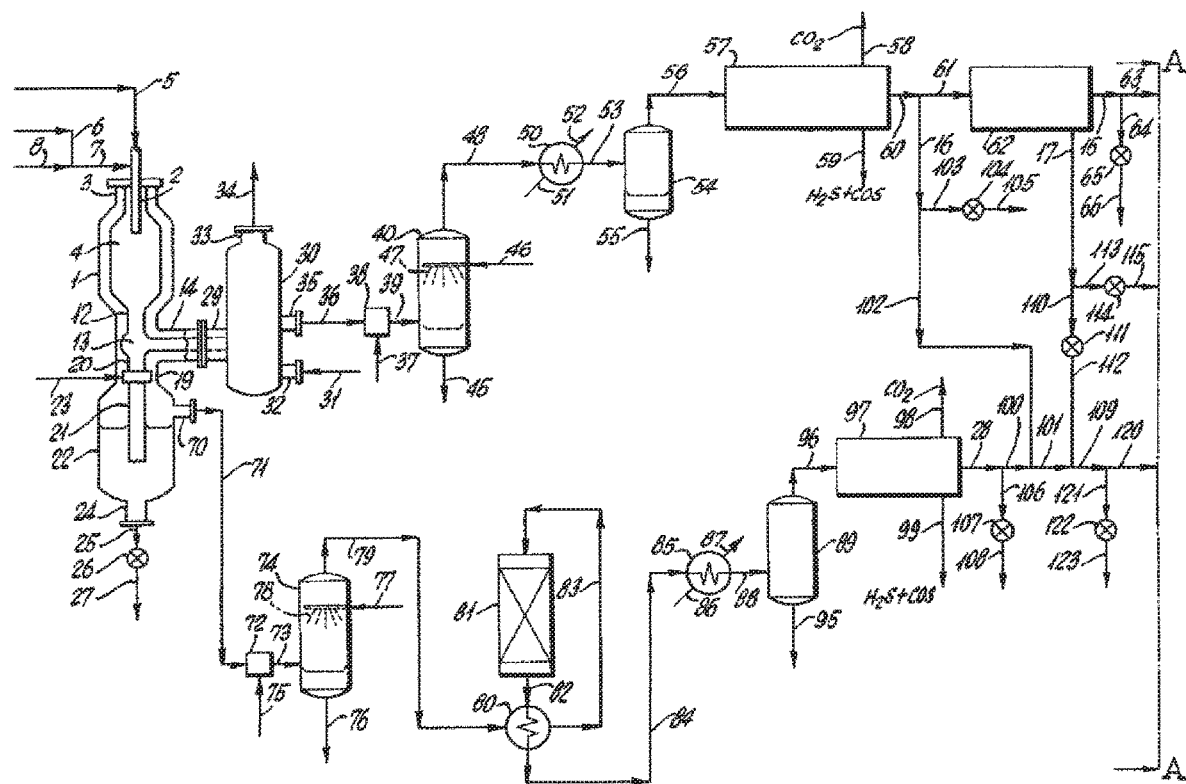
FIG. 1 is a the related art process flow diagram of U.S. Pat. No. 4,110,359.
Figure 2:
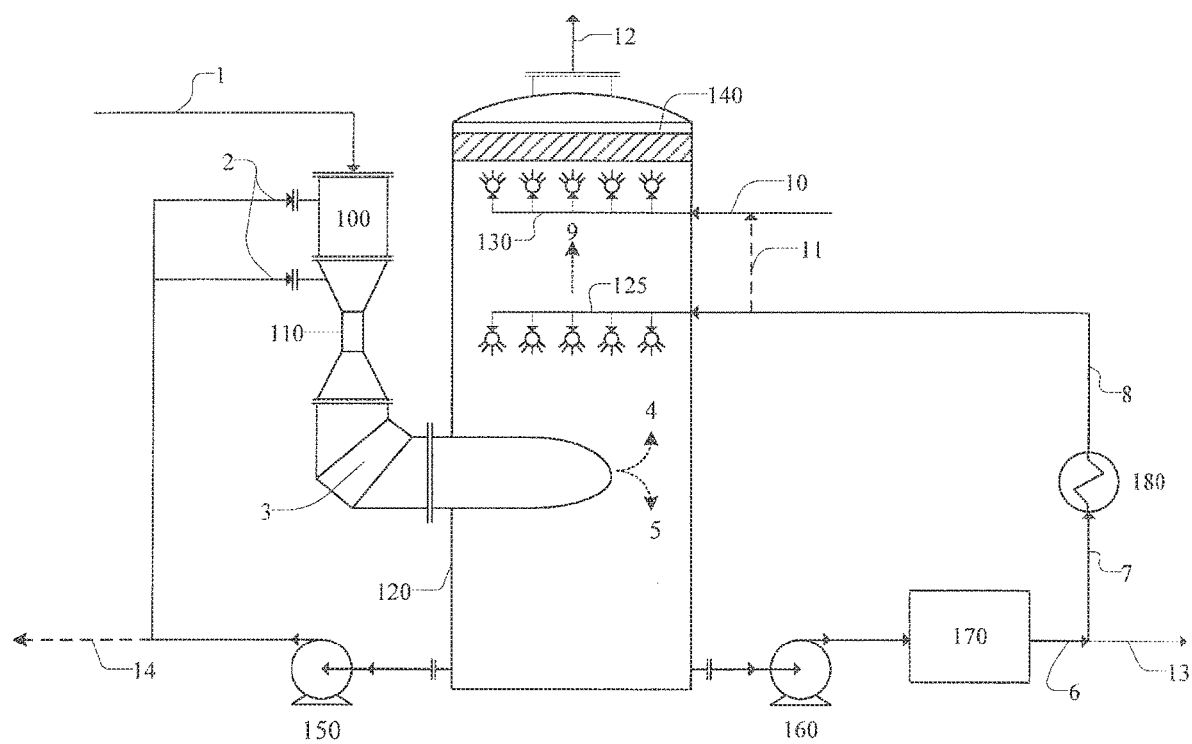
FIG. 2 illustrates the integrated process and operation unit for conditioning a soot-containing synthesis gas stream in accordance with one embodiment of the present invention.

With reference to the embodiment of FIG. 2 of the integrated process and unit operation of the present invention, hot raw soot-containing syngas stream (1) containing particulate matter and gaseous contaminants is routed to quenching device (100) where it is brought into intimate contact with a process water stream (2) such that the hot raw syngas is cooled, typically to a temperature in the range of about 250 to 400° F. The syngas stream is effectively saturated with water, containing atomized water droplets, and thereby forms a two-phase (i.e., liquid and gas) stream. This can be achieved by spraying the process water into the hot raw syngas stream in a manner similar to that described in U.S. Pat. No. 5,512,085. The quenched raw syngas and excess liquid water are then fed to a first orifice or Venturi-type first scrubber device (110) in which atomized water droplets collide forming small water droplets that wet and collect on the PM in the raw syngas creating much larger droplets that are easily disengaged from the gas stream. A process water stream (2) is introduced at a rate sufficient to effectively saturate the hot syngas stream (1) with water and provide atomized water droplets. The two phase stream (3) is then directed to the bottom of a second scrubbing vessel (120) to separate the essentially PM-free syngas (4) from the PM-laden process water (5). The bottom portion of the scrubbing vessel (120) is designed with the intent of not only separating the gas (having water-soluble contaminants) and liquid (contaminated with PM) phases but also effectively disengaging the entrained droplets from the syngas stream. The bottom portion can be a cyclonic separator or simply a large diameter vessel. Essentially all of the PM is removed from the syngas stream, typically greater than 98%, and concentrates in the circulating process water stream. A pump (150) is provided to return a first portion of process water in the bottom of the scrubbing vessel (120) to the quenching device (100) and the first scrubber device (110) via conduits (2).

A second portion of the PM-laden process water in the bottom of the scrubbing vessel (120) is routed to a filtration system (170) via pump (160) to remove PM producing a process water stream (6) that is substantially free of PM. A substantial portion of the PM-free process water (7) is cooled in an indirect heat exchanger (180) to a temperature in the range of about ambient to 150° F. and brought into intimate contact with the PM-free syngas (4) in the top portion of the scrubbing vessel (120).

As shown in FIG. 2, intimate contact is achieved by spraying the cooled process water (8) directly into the PM-free syngas (4) via a spray nozzle device (125). Direct contact cooling effectively reduces the temperature of the gas stream below its dew point leading to a substantial reduction in the water content of the PM-free syngas. In addition, water-soluble contaminants, remaining entrained PM, and entrained water droplets are effectively scrubbed from the PM-free syngas. The flow rate of the cooled process water stream (8) is set such that the temperature of the cleaned and cooled syngas (9) is reduced below the dew point and preferably below 150° F. and that essentially all of the $NH_3$ in the syngas is scrubbed. The cooled and cleaned syngas (9) passes through a mist eliminating device (140) disposed at a top of the scrubbing vessel (120), and above spray nozzle device (125) to remove entrained water droplets. A second set of spray nozzles (130) may be included to wash the surface of the mist eliminating device (140) to ensure that it remains wet and free of PM. Fresh make-up water (10) and or cooled, PM-free process water (11) can be used as the wash water. Fresh water (10) preferably being a high-quality water containing no dissolved gases, for example a deaerated reverse osmosis (RO)-quality water stream, in the temperature range of ambient to 150° F. is preferred as it will be PM free and contain no water-soluble contaminants (e.g., $NH_3$ and HCN) thus providing a final scrubbing of the syngas stream.

The transfer of heat, particulate matter, and water soluble gases can be promoted between the gas and liquid phases by the addition of structured packing, random packing, or trays located, but not shown, in the interstitial space below the spray nozzle devices (125) and/or (130).

After passing through the mist eliminating device (140), the cooled and cleaned syngas (12) is suitable for downstream processing. The cooled and cleaned syngas (12) streams will have a temperature in the range of about ambient to 150° F., and preferably 100° F. to 140° F., a pressure in the range of about 1 to 600 psig, and preferably 300 to 500 psig. The gas composition of the hot raw syngas stream by volume on a dry basis is as follows: 50 to 75% $H_2$, 20 to 45% CO, 1 to 10% $CO_2$, 0.1 to 5% $CH_4$, 0-1% $N_2$, 0-1% Ar, 0-1% of small hydrocarbons including, for example. $C_2H_2$, $C_2H_4$, $C_2H_6$, $C_3H_6$, 0 to 5 ppmv $NH_3$, 0 to 100 ppmv HCN, 0 to 10 ppmv $H_2S$, and 0 to 5 ppmv COS. The cleaned and cooled syngas stream may also contain 0 to 10 mg/Nm3 of particulate matter.

Since the cleaned and cooled syngas (12) has a lower water content than the hot, raw syngas (1), water is produced and must be extracted from the scrubbing vessel (120) to maintain a neutral water balance. In the system of this embodiment, process water (13) is withdrawn from the process. Process water exits the syngas conditioning section and is either recycled to a dirty steam system for generation of process steam, sent to a high-pressure process condensate stripper for production of a clean steam product, or sent to a waste water system for disposal. Alternatively, a portion of the PM-laden process water (2) can be withdrawn from the process via (14) and routed to other process sections for example to a gasifier quench, filtration system or process waste water treatment system for disposal.

The temperature of the accumulated process water in the second scrubbing vessel (120) is preferentially maintained below 150° F. such that a significant portion of the water-soluble contaminants, particularly $NH_3$, can be essentially removed due to the high solubility of $NH_3$ in water and particularly cold water. $NH_3$ will be scrubbed from the syngas stream in the direct contact cooling zone of soot scrubber (120) and accumulates in the circulating process water.

Filtration system (170) can be any number of suitable physical separation processes including for example mechanical filters or hydrocyclones coupled with filters. The location of the filtration system (170) is provided only as an example and numerous other locations and variations on relative position and number of the filter devices could be arranged. Filtration, or physical separation, of the PM from the process water enables the combining of (i.e., soot water and process condensate) and reuse of the entire process water stream in clean or dirty steam systems, which effectively eliminates a waste water product from the syngas conditioning system compared to prior art processes. Further, filtration is beneficial as it decouples PM removal from the level control in the scrubbing vessel (120), which is also used to maintain the water balance in the syngas conditioning system.

The addition of a particulate matter removal device (170) decouples particulate matter removal and waste water rejection mechanism. Particulate matter removal and waste water rejection are decoupled as particulate matter is removed from the process by a mechanical means that is independent of the disposal of waste water. This has the effect of dramatically reducing the amount of waste water rejected from the process and further, a significant reduction in the amount of fresh, high-quality make up water (10) can be realized.

Figure 3:
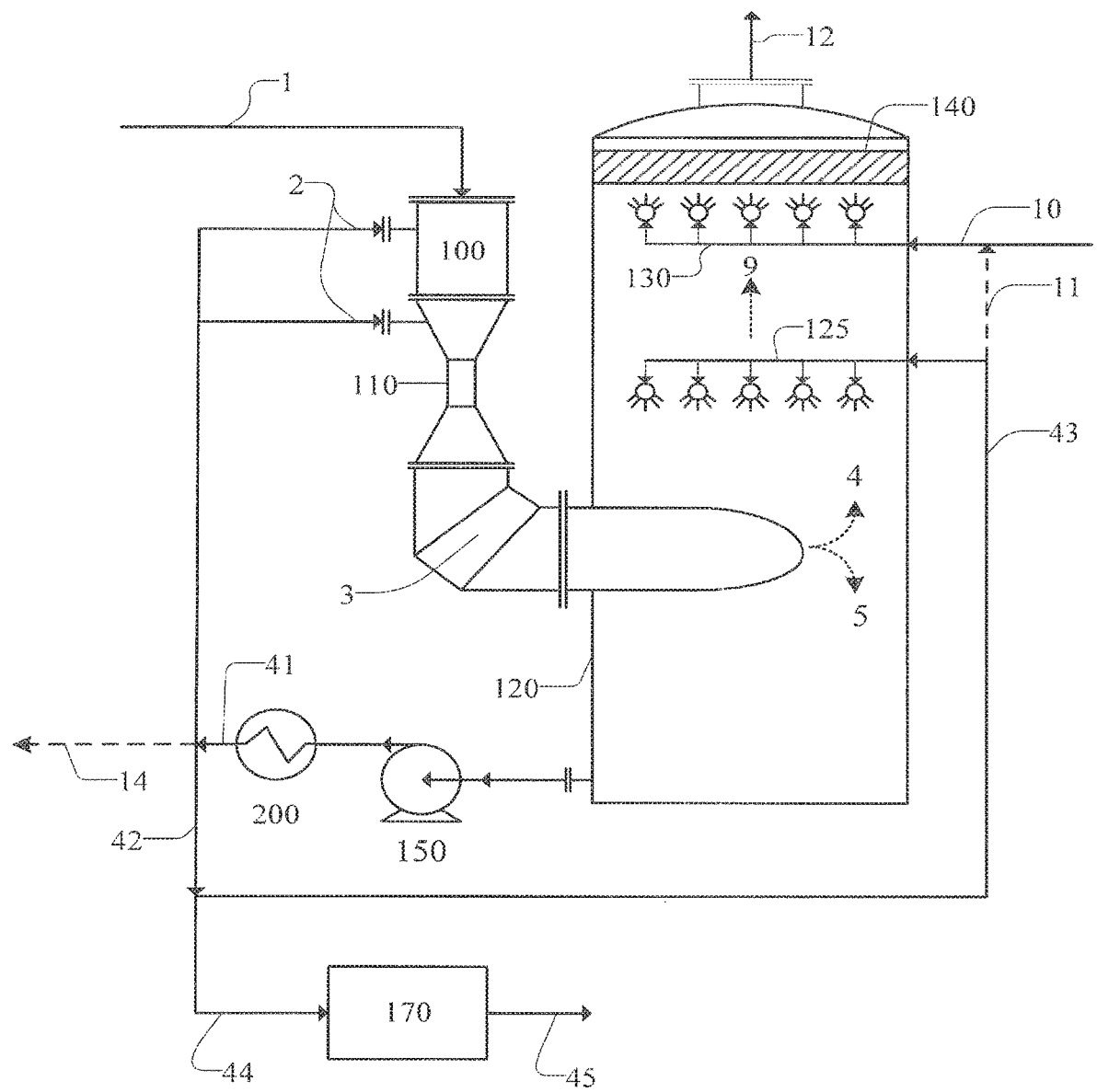
FIG. 3 is a process flow diagram of illustrating another embodiment of the integrated process and operation unit of the present invention.

In an alternate embodiment of the present invention, and as illustrated in FIG. 3, PM-laden process water is extracted from the bottom of the second scrubbing vessel (120) via a pump (150) and cooled in an indirect heat exchanger (200) such that the temperature of stream 41 is in the range of about ambient to 150° F. The cooled PM-laden stream (41) is split with a portion being returned to the quenching device (100) via conduit (2), and a portion (42) being further split with a large portion (43), which is returned to the top portion of the scrubbing vessel (120). On the other hand, a smaller portion (44) is routed to filtration system (170) to remove PM, producing a process water stream (45) that is substantially free thereof. The filtration system (170) is optional.

Figure 4:
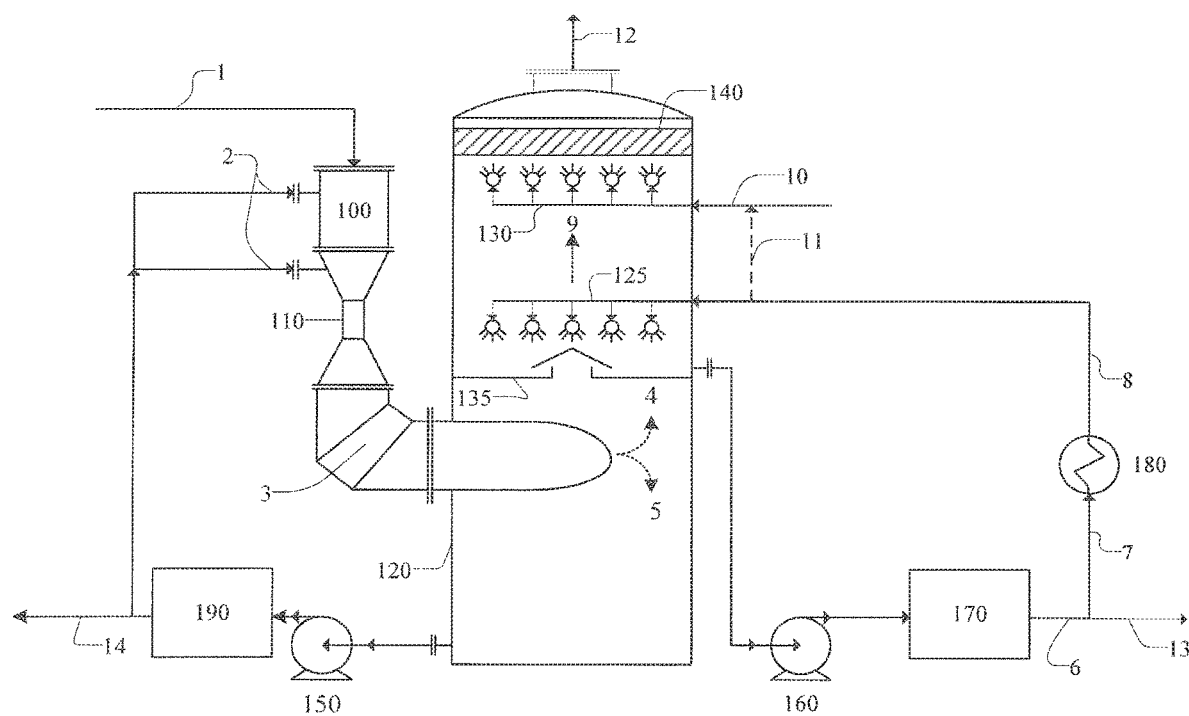
FIG. 4 depicts another embodiment of the of the integrated process and operation unit of the present invention.

Another exemplary embodiment of the integrated process and unit operation is shown with reference to FIG. 4. The process is very similar to that provided in FIG. 2, where the addition of a mechanism for physically separating (135) the PM-laden process water in the bottom portion of the scrubbing column (120) and the essentially PM-free cooling and scrubbing water in the top portion of the scrubbing column. The addition this device (135) enables the scrubbing column to achieve all of the process steps (PM scrubbing, gas cooling, condensate knockout, and $NH_3$ scrubbing) while separating the two process water streams. This decouples the rate of accumulation of PM and water-soluble contaminants thus allowing for independent control of the concentration of these contaminants. This separation means (135) can be a stove pipe, a stage separator or the like. A filtration system (190) is included in conduit (2) to remove particulate matter from the first portion of process water from the bottom of the scrubbing vessel (120) prior to being returned to the quenching device (100) and the first scrubber device (110) via conduits (2). A portion of the process water exiting the filtration device (190) is withdrawn from the process via (14) and routed to other process sections for example to a gasifier quench or process waste water treatment system for disposal. The addition of filtration device (190) provides a means of independently maintaining the water balance via stream 14 and the accumulation of water soluble contaminants in the process water via stream 13.

While the invention has been described in detail with reference to specific embodiments thereof, it will become apparent to one skilled in the art that various changes and modifications can be made, and equivalents employed, without departing from the scope of the appended claims.

What is claimed is:

1. An integrated process for conditioning a soot-containing synthesis gas stream, comprising:
   (a) introducing a raw soot-containing synthesis gas having particulate matter and gaseous contaminants therein at a temperature of less than about 900° F. into a quenching device to reduce the temperature of said synthesis gas to a range of about 250-400° F., thereby forming a two-phase stream;
   (b) routing the two-phase stream through a first scrubber device to substantially transfer majority of particulate matter from the gas phase to the liquid phase;
   (c) directing said two-phase stream to a second scrubbing device wherein the two-phase stream is separated into a liquid-phase fluid contaminated with particulate matter and a gas-phase fluid having water-soluble contaminants at a lower section of the scrubbing device;
   (d) cleaning and cooling the gas-phase fluid having water-soluble contaminants in an upper section of the second scrubbing device where the gas-phase fluid comes in direct contact with process water cooled to a temperature below 150° F. dispensed through a spray nozzle device thereby reducing the temperature of the gas phase fluid below the dew point temperature and removing water soluble impurities and remaining particulate matter therefrom;
   (e) further routing the cooled and cleaned gas phase fluid of step (d) through a mist eliminating device disposed in the upper section of the second scrubbing device to remove substantially all of the remaining entrained water droplets, thereby producing a cooled and substantially soot-free synthesis gas stream.

2. The integrated process of claim 1, further comprising: recycling at least a portion of said liquid-phase fluid contaminated with particulate matter from said second scrubbing device to said quenching device.

3. The integrated process of claim 1, further comprising removing at least a portion of the liquid-phase fluid with particulate matter from said second scrubbing device, pumping it through a filtration device, removing the particulate matter and recycling at least a portion of a clean process water stream to the spray nozzle device disposed in the second scrubbing device.

4. The integrated process of claim 3, wherein the portion of said clean process water stream routed to the spray nozzle is routed through a heat exchanger and cooled to about 150° F.

5. The integrated process of claim 4, further providing another portion of said clean process water to a second set of spray nozzles in communication with said mist eliminating device.

6. The integrated process of claim 1, wherein the raw soot-containing synthesis gas has a composition by volume on a dry basis by volume: 50 to 75% $H_2$, 20 to 45% CO, 1 to 10% $CO_2$, 0.1 to 5% $CH_4$, 0-1% $N_2$, 0-1% Ar, 0-1% of small hydrocarbons.

7. The integrated process of claim 1, wherein the raw soot-containing synthesis gas includes 0 to 500 mg/$Nm^3$ of particulate matter consisting primarily of soot derived from the hydrocarbon feedstock and refractory dust from upstream process equipment.

8. The integrated process of claim 1, wherein the raw soot-containing synthesis gas is at a pressure ranging from about 1 to 600 psig.

9. The integrated process of claim 1, wherein the substantially soot-free synthesis gas stream has a temperature in the range of about ambient temperatures to 150° F., a pressure in the range of about 1 to 600 psig and a particulate contaminant of about 0 to 10 mg/$Nm^3$.

10. The integrated process of claim 1, wherein substantially all of the $NH_3$ is removed from the substantially soot free synthesis gas stream and the remaining water-soluble impurities including HCN, CHOOH, HCl, $H_2S$, COS are partially removed from the syngas stream in the second scrubbing device.

11. The integrated process of claim 2, further comprising routing a portion of the liquid-phase fluid contaiminated with particulate matter to said first scrubbing device.

* * * * *